US009309190B2

(12) United States Patent
Gharda

(10) Patent No.: US 9,309,190 B2
(45) Date of Patent: Apr. 12, 2016

(54) PROCESS FOR PREPARATION OF DICYANOCARBOXYLATE DERIVATIVES

(71) Applicant: Keki Hormusji Gharda, Bandra (West) Mumbai (IN)

(72) Inventor: Keki Hormusji Gharda, Bandra (West) Mumbai (IN)

( * ) Notice: Subject to any disclaimer, the term of this patent is extended or adjusted under 35 U.S.C. 154(b) by 0 days.

(21) Appl. No.: 14/062,247

(22) Filed: Oct. 24, 2013

(65) Prior Publication Data
US 2014/0051881 A1 Feb. 20, 2014

Related U.S. Application Data

(63) Continuation of application No. PCT/IN2012/000149, filed on Feb. 2, 2012.

(30) Foreign Application Priority Data

Apr. 25, 2011 (IN) .......................... 1297/MUM/2011

(51) Int. Cl.
C07C 253/30 (2006.01)
C07C 255/19 (2006.01)
C07C 253/10 (2006.01)

(52) U.S. Cl.
CPC .............. *C07C 253/30* (2013.01); *C07C 253/10* (2013.01); *C07C 255/19* (2013.01)

(58) Field of Classification Search
CPC .............................. C07C 255/19; C07C 253/30
USPC ......................................................... 558/443
See application file for complete search history.

(56) References Cited

U.S. PATENT DOCUMENTS 4,182,823 A * 1/1980 Schoenberg .................. 526/298

FOREIGN PATENT DOCUMENTS

| AU | 725472 | 1/2001 |
| CN | 1785966 | 6/2006 |
| CN | 1887872 | 1/2007 |
| CN | 101203134 | 6/2008 |
| CN | 101600696 | 12/2009 |
| EP | 0234119 | 9/1987 |
| EP | 0295117 | 12/1998 |
| IN | 129MUM2010 | 1/2010 |
| WO | 93/06089 | 4/1993 |
| WO | 2005/023773 | 3/2005 |
| WO | 2006/134459 | 12/2006 |
| WO | WO 2010129068 A1 * | 11/2010 |
| WO | WO 2011086570 A1 * | 7/2011 |

OTHER PUBLICATIONS

Carrie, R. "Preparation of Substituted Dicyano-2,3 Ethyl Propanoates and Study of Their Hydrolysis Mechanism, Production of Corresponding Succinic Acids and Several Nitrogenized Derivatives" Bulletin de la Societe Scientifique de Bretagne 1962, 37, 29-58.*

Carrie, R. Bulletin de la Societe Scientifique de Bretagne 1962, 37, 29-58, English Human Translation obtained from the United States Patent and Trademark Office, Washington, D.C. Oct. 2014, Translated by: Schreiber Translations, Inc.*
"Occupational Exposure to Hydrogen Cyanide and Cyanide Salts (NaCN, KCN, and Ca(Cn)2)," Occupational Exposure to Hydrogen Cyanide and Cyanide Salts, vol. 99. National Institute for Occupational Safety and Health. Division of Criteria Documentation and Standards Development. 1976, p. 39.*
Lapworth et al. "Phenylsuccinic Acid" Org. Synth. 1928, 8, 88.*
Nagata et al. "Hydrocyanation of Conjugated Carbonyl Compounds" Organic Reactions 1977, vol. 25, ch. 3, 255-476.*
Chatterjee, Asima, et al. "Unusual Cyclization of Ethyl a,B-Dicyano-p-methoxydihydrocinnamate with Polyphosphoirc Acid." Indian Journal of Chemistry. vol. 17B, No. 6. Jun. 1979. pp. 541-542.
Das, Sarmistha, et al. "Total synthesis and anaglesic activity of 6-fluoroindan-1-carboxylic acid." Tetrahedron. vol. 64, No. 37. 2008. pp. 8642-8645.
Higson, Annie and Jocelyn Field Thorpe. "A Method for the Formation of Succinic Acid and of its Alkyl Derivatives." Journal of Chemical Society. 1906. pp. 1455-1472.
Lange, J., et al. "Synthesis and Properties of New Cyclic Derivatives of Succinic Acid with Anticonvulsant Activity." Pharmazie. vol. 64, No. 37. Jul. 8, 2009. pp. 8642-8645.
Smith, Peter A. S. and Jermome P. Horwitz. "A Synthesist for Unsymmetrically Substituted Succinic Acids." Journal of American Chemical Society. 1949. pp. 3418-3419.
Whiteley, R.V., Jr. and R.S. Marianelli. "The Synthesis of 2,3 Disubstituted Succinodinitriles." Synthesis. 1978. pp. 392-394.
International Search Report issued in corresponding international application No. PCT/IN2012/000149 on Sep. 13, 2012.

* cited by examiner

Primary Examiner — Nyeemah A Grazier
Assistant Examiner — Amanda L Aguirre
(74) Attorney, Agent, or Firm — Whiteford, Taylor & Preston, LLP; Peter J. Davis

(57) ABSTRACT

The present disclosure provides a process for preparing 2,3-dicyanopropionic acid ester of formula (I); said process comprising the following steps: i) treating an alkali metal cyanide dissolved in a solvent with a solution of 2-cyano-2-propenoic acid ester of formula (II) at a temperature ranging between 0° C. and 50° C. for a time period ranging between 2 hours and 15 hours followed by cooling below 20° C. to obtain a sodium salt of 2,3-dicyanopropionic acid ester of formula (I); and

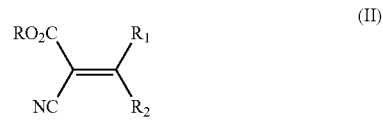

ii) neutralizing the sodium salt of 2,3-dicyanopropionic acid ester using a neutralizing agent to obtain a 2,3-dicyanopropionic acid ester of formula (I).

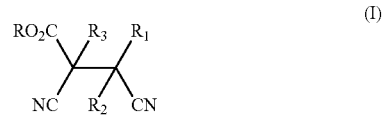

9 Claims, No Drawings

PROCESS FOR PREPARATION OF DICYANOCARBOXYLATE DERIVATIVES

CROSS REFERENCE TO RELATED APPLICATIONS

This application is a continuation of International Application No. PCT/IN2012/000149, filed Feb. 2, 2012, which claims priority to Indian Patent Application No. 1297/MUM/2011, filed Apr. 25, 2011, the specifications of which are incorporated herein by reference in their entirety.

FIELD OF THE INVENTION

The present disclosure relates to a process for preparing dicyanocarboxylate derivatives.

BACKGROUND 2,3-Dicyanopropionate derivatives are widely used for the synthesis of pyrazole derivatives. Pyrazole derivatives have application in the manufacture of fine chemicals and agrochemicals which has pesticidal or insecticidal properties as described in European Patent Publication Nos. 0295117 and 0234119 and WO93/06089

Ethyl 2,3-dicyanopropionate was first prepared by Higson and Thorpe (Journal of Chemical Society, 89, 1460 (1906)) by reacting formaldehyde cyanohydrin with sodium salt of ethyl cyanoacetate. The reaction is represented below.

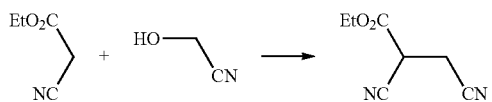

The process disclosed by Higson and Thorpe for preparing ethyl 2,3-dicyanopropionate suffers from a significant drawback such as the formaldehyde cyanohydrin used as a reactant is less stable, polymerizes easily in presence of alkali and undergoes spontaneous and violent decomposition.

The preparation of 2,3-dicyanopropionates is disclosed by Smith and Horwitz (Journal of American Chemical Society, 1949, 21, 3418). The process discloses the formation and isolation of 3-substituted-2,3-dicyanopropionates as an intermediate in the preparation of 2,3-disubstituted succinodinitriles from cyanoacetate, ketones and potassium cyanide.

Further, Whiteley and Marianelli (Synthesis (1978), 392) disclosed a process for preparing 3-substituted-2,3-dicyanopropionates as an intermediate in the preparation of 2,3-disubstituted succinodinitriles from cyanoacetate, aldehydes ($C_1$-$C_3$ alkylaldehyde or benzaldehyde) and potassium cyanide.

Australian Patent No. 725472 discloses synthesis of ethyl 2,3-dicyano propionate by reacting potassium cyanide with ethyl cyanoacetate and para-formaldehyde in ethanol to obtain a potassium salt of ethyl 2,3-dicyano propionate. The potassium salt on dissolution in water, acidification to pH 4 and extraction with dichloromethane provides 2,3-dicyano ethyl propionate.

Chinese Patent No. 1785966 discloses a reaction of ethyl cyanoacetate, para-formaldehyde and sodium cyanide to synthesize ethyl-2,3-dicyano-propionate in dimethyl sulfoxide. The obtained ethyl-2,3-dicyano propionate is further purified. Indian Application No. 129/MUM/2010 discloses a process for the preparation of ethyl-2,3-dicyano-propionate which involves reacting an alkali metal cyanide and para-formaldehyde in the presence of a solvent to obtain glycolonitrile and reacting the glycolonitrile in-situ with an alkali ethoxide and cyanoacetate to obtain ethyl-2,3-dicyanopropionate derivatives.

The methods for the synthesis of cyanoalkylpropionate derivatives as disclosed in the prior art suffer significant drawback in that it is first necessary to extract or isolate the intermediate formaldehyde cyanohydrin (glycolonitrile), which is highly water soluble. The isolation of cyanohydrin involves a tedious and lengthy continuous extraction process (counter current extraction with polar solvent such as ether). Further, formaldehyde cyanohydrin has a limited stability and often gets decomposed violently upon attempted distillation. Furthermore, the reaction requires care given the risk of formation of dimeric side-products.

In view of the above, there is envisaged in accordance with the present disclosure an economic, high yielding and simple process for preparing 2,3-dicyanopropionic acid ester.

OBJECTS OF THE PRESENT INVENTION

Some of the objects of the present disclosure are as follows:

It is an object of the present disclosure to provide a process for preparing 2,3-dicyanopropionic acid esters.

It is another object of the present disclosure to provide a process for preparing 2,3-dicyanopropionic acid esters which is simple, economic and high yielding.

It is still another object of the present disclosure to provide a process for preparing highly pure 2,3-dicyanopropionic acid esters.

It is yet another object of the present disclosure to provide a process which employs stable reactants.

SUMMARY OF THE PRESENT INVENTION

These and other objects of the present disclosure are to a great extent dealt in the disclosure.

In one aspect of the present disclosure there is provided a process for preparing 2,3-dicyanopropionic acid ester of formula (I); said process comprising the following steps:

i) treating an alkali metal cyanide in a solvent with a solution of 2-cyano-2-propenoic acid ester of formula (II) at a temperature ranging between 0° C. and 50° C. for a time period ranging between 2 hours and 15 hours followed by cooling below 20° C. to obtain a sodium salt of 2,3-dicyanopropionic acid ester of formula (I); and

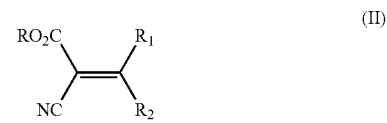

wherein, R is selected from the group consisting of $C_1$-$C_{20}$ straight or branched chain alkyl substituents, substituted or unsubstituted aromatic substituents and aliphatic substituents; and $R_1$ and $R_2$ are independently selected from the group consisting of hydrogen, $C_1$-$C_{20}$ straight or branched chain alkyl substituents, substituted or unsubstituted aromatic substituents and aliphatic substituents, ii) neutralizing the sodium salt of 2,3-dicyanopropionic acid ester using a neutralizing agent to obtain a 2,3-dicyanopropionic acid ester of formula (I),

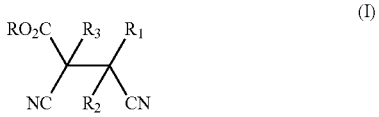

10 wherein, R is selected from the group consisting of C$_1$-C$_{20}$ straight or branched chain alkyl substituents, substituted or unsubstituted aromatic substituents and aliphatic substituents;
R$_1$ and R$_2$ are independently selected from the group consisting of hydrogen, C$_1$-C$_{20}$ straight or branched chain alkyl substituents, substituted or unsubstituted aromatic substituents and aliphatic substituents; and
R$_3$ is hydrogen.

Typically, the process is a single pot reaction.

In one embodiment of the present disclosure there is provided a process for preparing 2,3-dicyanopropionic acid ester of formula (I); said process comprising the following steps:
i) adding an alkali metal cyanide to a solvent followed by stirring at a temperature ranging between 0° C. and 50° C. for a time period ranging between 2 hours and 8 hours to obtain a slurry;
ii) injecting a solution of 2-cyano-2-propenoic acid ester of formula (II) into the slurry at a temperature ranging between 0° C. and 50° C. for a time period ranging between 2 hours and 8 hours to obtain a reaction mixture;

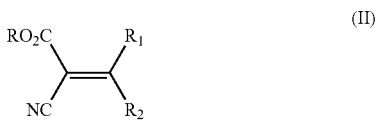

wherein, R is selected from the group consisting of C$_1$-C$_{20}$ straight or branched chain alkyl substituents, substituted or unsubstituted aromatic substituents and aliphatic substituents; and
R$_1$ and R$_2$ are independently selected from the group consisting of hydrogen, C$_1$-C$_{20}$ straight or branched chain alkyl substituents, substituted or unsubstituted aromatic substituents and aliphatic substituents,
iii) stirring the reaction mixture at a temperature ranging between 0° C. and 50° C. for a time period ranging between 2 hours and 15 hours followed by cooling below 20° C. to obtain a sodium salt of 2,3-dicyanopropionic acid ester of formula (I); and
iv) neutralizing the sodium salt of 2,3-dicyanopropionic acid ester using a neutralizing agent to obtain a 2,3-dicyanopropionic acid ester of formula (I),

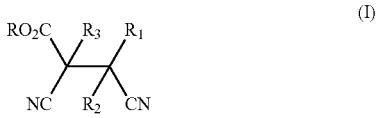

wherein, R is selected from the group consisting of C$_1$-C$_{20}$ straight or branched chain alkyl substituents, substituted or unsubstituted aromatic substituents and aliphatic substituents;
R$_1$ and R$_2$ are independently selected from the group consisting of hydrogen, C$_1$-C$_{20}$ straight or branched chain alkyl substituents, substituted or unsubstituted aromatic substituents and aliphatic substituents; and
R$_3$ is hydrogen.

In accordance with one preferred embodiment of the present disclosure the process for preparing 2,3-dicyanopropionic acid ester of formula (I) comprises a method step of adding the slurry of alkali metal cyanide into the solution of 2-cyano-2-propenoic acid ester of formula (II) at a temperature ranging between 0° C. and 50° C. for a time period ranging between 2 hours and 8 hours.

The process in accordance with the present disclosure further comprises a pre-step of stabilizing 2-cyano-2-propenoic acid ester of formula (II) using a stabilizing agent.

Typically, the stabilizing agent is at least one selected from the group consisting of methanesulfonic acid, methanesulfonic anhydride, trifluoromethane sulfonic acid, trifluoromethane sulfonic anhydride, trichloromethane sulfonic acid, trichloromethane sulfonic anhydride, tribromomethane sulfonic acid, tribromomethane sulfonic anhydride, substituted or unsubstituted aromatic sulfonic acids, substituted or unsubstituted aromatic sulfonic anhydrides, hydroquinone, alkyl substituted hydroquinone, phosphorous pentoxide and C$_1$-C$_{14}$ aliphatic carboxylic acids.

Preferably, the stabilizing agent is methanesulfonic acid.

Typically, the amount of stabilizing agent ranges between 0.1 and 15% of the mass of 2-cyano-2-propenoic acid ester of the formula (II).

Preferably, the amount of stabilizing agent ranges between 1.0 and 10% of the mass of 2-cyano-2-propenoic acid ester of the formula (II).

In accordance with present disclosure the alkali metal cyanide is at least one selected from the group consisting of sodium cyanide, potassium cyanide and lithium cyanide.

Preferably, the alkali metal cyanide is sodium cyanide.

Typically, the solvent is at least one selected from the group consisting of C$_1$-C$_{14}$ aliphatic alcohols, aromatic alcohols, acetonitrile, dimethylsulfoxide, sulfolane, dimethylformamide, ethylenedichloride, methylenedichloride, N-methyl pyrrolidone, monoglyme, diglyme, 2-methoxyethanol, 2-ethoxyethanol, 2-butoxyethanol and N—N'-dimethylimidazolidone.

Preferably, the solvent is ethanol.

Typically, the proportion of the solvent ranges between 500 ml and 1000 ml per mole of 2-cyano-2-propenoic acid ester of formula (II).

Preferably, the proportion of the solvent ranges between 500 ml and 700 ml per mole of 2-cyano-2-propenoic acid ester of formula (II).

Typically, the neutralizing agent is at least one selected from the group consisting of hydrogen chloride, C$_1$-C$_{14}$ aliphatic acids and aromatic acids.

Typically, the 2-cyano-2-propenoic acid ester of formula (II) is selected from the group consisting of 2-cyano-2-propenoic acid methyl ester, 2-cyano-2-propenoic acid ethyl ester, 2-cyano-2-propenoic acid isopropyl ester and 2-cyano-2-propenoic acid propyl ester.

Preferably, the 2-cyano-2-propenoic acid ester of formula (II) is 2-cyano-2-propenoic acid ethyl ester.

Typically, the 2,3-dicyanopropionic acid ester of formula (I) is selected from the group consisting of 2,3-dicyanopropionic acid methyl ester, 2,3-dicyanopropionic acid ethyl ester, 2,3-dicyanopropionic acid isopropyl ester and 2,3-dicyanopropionic acid propyl ester.

Preferably, the 2,3-dicyanopropionic acid ester of formula (I) is 2,3-dicyanopropionic acid ethyl ester.

In accordance with another aspect of the present disclosure there is provided 2,3-dicyanopropionic acid ester of formula I prepared by a process of the present disclosure,

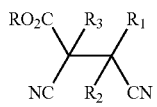
(I)

wherein, R is selected from the group consisting of $C_1$-$C_{20}$ straight or branched chain alkyl substituents, substituted or unsubstituted aromatic substituents and aliphatic substituents;

$R_1$ and $R_2$ are independently selected from the group consisting of hydrogen, $C_1$-$C_{20}$ straight or branched chain alkyl substituents, substituted or unsubstituted aromatic substituents and aliphatic substituents; and $R_3$ is hydrogen.

DETAILED DESCRIPTION OF THE INVENTION

The inventors of the present disclosure developed a process that overcomes the drawback associated with the use of formaldehyde cyanohydrin and para-formaldehyde as reactants. The process of the present disclosure totally eliminates the possibility of formation of dimerisation side product, thereby obtaining the product having high purity and yield.

In accordance with the present disclosure there is provided a process for preparing 2,3-dicyanopropionic acid ester of formula (I).

In one embodiment of the present disclosure there is provided a one pot process for preparing 2,3-dicyanopropionic acid ester of formula (I).

Initially, an alkali metal cyanide in a solvent is treated with a solution of 2-cyano-2-propenoic acid ester of formula (II). The treating is carried out at a temperature ranging between 0° C. and 50° C. for a time period ranging between 2 hours and 15 hours. After the completion of treating the treated mass is cooled below 20° C. to obtain a sodium salt of 2,3-dicyanopropionic acid ester of formula (I).

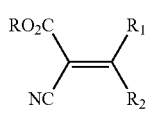
(II)

wherein, R is selected from the group consisting of $C_1$-$C_{20}$ straight or branched chain alkyl substituents, substituted or unsubstituted aromatic substituents and aliphatic substituents; and $R_1$ and $R_2$ are independently selected from the group consisting of hydrogen, $C_1$-$C_{20}$ straight or branched chain alkyl substituents, substituted or unsubstituted aromatic substituents and aliphatic substituents, Then the sodium salt of 2,3-dicyanopropionic acid ester is neutralized using a neutralizing agent to obtain a 2,3-dicyanopropionic acid ester of formula (I),

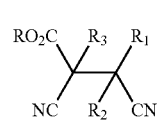
(I)

wherein, R is selected from the group consisting of $C_1$-$C_{20}$ straight or branched chain alkyl substituents, substituted or unsubstituted aromatic substituents and aliphatic substituents;

$R_1$ and $R_2$ are independently selected from the group consisting of hydrogen, $C_1$-$C_{20}$ straight or branched chain alkyl substituents, substituted or unsubstituted aromatic substituents and aliphatic substituents; and $R_3$ is hydrogen.

In another embodiment of the present disclosure following process is provided for preparing 2,3-dicyanopropionic acid ester of formula (I).

In the first step, alkali metal cyanide is added to a solvent followed by stirring. The stirring is carried out at a temperature ranging between 0° C. and 50° C. for a time period ranging between 2 hours and 8 hours to obtain a slurry.

The alkali metal cyanide includes but is not limited to sodium cyanide, potassium cyanide and lithium cyanide. The preferred alkali metal cyanide is sodium cyanide. The solvent used is selected from the group consisting of $C_1$-$C_{14}$ aliphatic alcohols, aromatic alcohols, acetonitrile, dimethylsulfoxide, sulfolane, dimethylformamide, ethylenedichloride, methylenedichloride, N-methylpyrrolidone, monoglyme, diglyme, 2-methoxyethanol, 2-ethoxyethanol, 2-butoxyethanol and N—N'-dimethylimidazolidone and combinations thereof. Amongst various solvents, ethanol is preferred.

In the second step, a solution of 2-cyano-2-propenoic acid ester of formula (II) is injected into the slurry. The injection is carried out at a temperature ranging between 0° C. and 50° C. for a time period ranging between 2 hours and 8 hours to obtain a reaction mixture. The 2-cyano-2-propenoic acid ester of formula (II) is represented below:

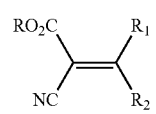
(II)

wherein, R is selected from the group consisting of $C_1$-$C_{20}$ straight or branched chain alkyl substituents, substituted or unsubstituted aromatic substituents and aliphatic substituents; and $R_1$ and $R_2$ are independently selected from the group consisting of hydrogen, $C_1$-$C_{20}$ straight or branched chain alkyl substituents, substituted or unsubstituted aromatic substituents and aliphatic substituents, In still another embodiment of the present disclosure the slurry of alkali metal cyanide is added into the solution of 2-cyano-2-propenoic acid ester of formula (II). The addition is carried out at a temperature ranging between 0° C. and 50° C. for a time period ranging between 2 hours and 8 hours.

In accordance with the present disclosure the proportion of the solvent is maintained between 500 ml and 1000 ml per mole of 2-cyano-2-propenoic acid ester of formula (II). The preferred proportion of the solvent is ranging between 500 ml and 700 ml per mole of 2-cyano-2-propenoic acid ester of formula (II).

The obtained reaction mixture is then stirred at a temperature ranging between 0° C. and 50° C. for a time period ranging between 2 hours and 15 hours followed by cooling below 20° C. to obtain a sodium salt of 2,3-dicyanopropionic acid ester of formula (I). The sodium salt of 2,3-dicyanopropionic acid ester is then neutralized using a neutralizing agent to obtain a 2,3-dicyanopropionic acid ester of formula (I). The neutralizing agent includes but is not limited to hydrogen chloride, $C_1$-$C_{14}$ aliphatic acids and aromatic acids.

The 2-cyano-2-propenoic acid ester of formula (II) for the preparation of 2,3-dicyanopropionic acid ester is used as such or it is first stabilized using a stabilizing agent. The stabilizing agent includes but is not limited to methanesulfonic acid, methanesulfonic anhydride, trifluoromethane sulfonic acid, trifluoromethane sulfonic anhydride, trichloromethane sulfonic acid, trichloromethane sulfonic anhydride, tribromomethane sulfonic acid, tribromomethane sulfonic anhydride, substituted or unsubstituted aromatic sulfonic acids, substituted or unsubstituted aromatic sulfonic anhydrides, hydroquinone, alkyl substituted hydroquinone, phosphorous pentoxide and $C_1$-$C_{14}$ aliphatic carboxylic acids. Amongst various stabilizing agents, methanesulfonic acid is preferred for the stabilization of 2-cyano-2-propenoic acid ester of formula (II). The amount of stabilizing agent used is about 0.1 to 15% of the mass of 2-cyano-2-propenoic acid ester. Preferably, the amount of stabilizing agent used is about 1.0 to 10% of the mass of 2-cyano-2-propenoic acid ester.

The 2-cyano-2-propenoic acid ester of formula (II) includes but is not limited to 2-cyano-2-propenoic acid methyl ester, 2-cyano-2-propenoic acid ethyl ester, 2-cyano-2-propenoic acid isopropyl ester and 2-cyano-2-propenoic acid propyl ester. The 2-cyano-2-propenoic acid ethyl ester is the preferred 2-cyano-2-propenoic acid ester of formula (II).

The 2,3-dicyanopropionic acid ester of formula (I) includes but is not limited to 2,3-dicyanopropionic acid methyl ester, 2,3-dicyanopropionic acid ethyl ester, 2,3-dicyanopropionic acid isopropyl ester and 2,3-dicyanopropionic acid propyl ester. The 2,3-dicyanopropionic acid ethyl ester is the preferred 2,3-dicyanopropionic acid ester of formula (I).

In accordance with another aspect of the present disclosure there is provided a 2,3-dicyanopropionic acid ester of formula I prepared by a process of the present disclosure,

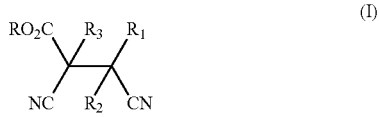

(I)

wherein, R is selected from the group consisting of $C_1$-$C_{20}$ straight or branched chain alkyl substituents, substituted or unsubstituted aromatic substituents and aliphatic substituents;

$R_1$ and $R_2$ are independently selected from the group consisting of hydrogen, $C_1$-$C_{20}$ straight or branched chain alkyl substituents, substituted or unsubstituted aromatic substituents and aliphatic substituents; and $R_3$ is hydrogen.

The present disclosure is further described in light of the following examples which are set forth for illustration purpose only and not to be construed for limiting the scope of the disclosure.

Example 1

0.6 liter of anhydrous ethanol and 51.46 gm of sodium cyanide (1.05 mole) were charged in a glass reactor equipped with a central vertical stirrer and a vertical condenser followed by stirring at 30° C. for 4 hours to obtain a slurry. Separately, 125.00 gm of 2-cyano-2-propenoic ethyl acid ester (1 mole) was stabilized with methanesulfonic acid (3 wt %) dissolved in 100 ml of ethanol to obtain a stabilized solution of 2-cyano-2-propenoic acid ethyl ester. The stabilized solution of 2-cyano-2-propenoic acid ethyl ester was injected into the slurry over 2 hours at 20° C. to 25° C. to obtain a reaction mixture. The reaction mixture was stirred further for 4 hours at 20° C. to 25° C. to obtain a reaction mass containing sodium salt of 2,3-dicyanopropionic acid ethyl ester. Reaction was monitored on the basis of unreacted sodium cyanide. Then the reaction mixture containing sodium salt of 2,3-dicyanopropionic acid ethyl ester was cooled to 10° C. and dry hydrogen chloride gas was bubbled to neutralize the sodium salt of 2,3-dicyanopropionic acid ethyl ester. The neutralized reaction mass was then subjected to vacuum distillation to distill ethanol. To the crude product obtained as a residue after distillation was added methylene dichloride and water below 10° C. and extracted. The organic layer containing the product and aqueous layer were separated. The organic layer was washed with water and then concentrated to obtain 2,3-dicyanopropionic acid ethyl ester in 85% yield (on purity basis).

Example 2

0.6 liter of anhydrous methanol and 51.46 gm of sodium cyanide (1.05 mole) were charged in a glass reactor equipped with a central vertical stirrer and a vertical condenser followed by stirring at 30° C. for 4 hours to obtain a slurry. Separately, 125.00 gm of 2-cyano-2-propenoic acid ethyl ester (1 mole) was stabilized with methanesulfonic acid (3 wt %) dissolved in 100 ml of methanol to obtain a stabilized solution of 2-cyano-2-propenoic acid ethyl ester. The stabilized solution of 2-cyano-2-propenoic acid ethyl ester was injected into the slurry over 2 hours at 20° C. to 25° C. to obtain a reaction mixture. The reaction mixture was stirred further for 4 hours at 20° C. to 25° C. to obtain a reaction mass containing sodium salt of 2,3-dicyanopropionic acid ethyl ester. Reaction was monitored on the basis of unreacted sodium cyanide. Then the reaction mixture containing sodium salt of 2,3-dicyanopropionic acid ethyl ester was cooled to 10° C. and dry hydrogen chloride gas was bubbled to neutralize the sodium salt of 2,3-dicyanopropionic acid ethyl ester. The neutralized reaction mass was then subjected to vacuum distillation to distill methanol. To the crude product obtained as a residue after distillation was added methylene dichloride and water below 10° C. and extracted. The organic layer containing the product and aqueous layer were separated. The organic layer was washed with water and then concentrated to obtain 2,3-dicyanopropionic acid ethyl ester in 45% yield (on purity basis).

Example 3

0.6 liter of anhydrous isopropanol and 51.46 gm of sodium cyanide (1.05 mole) were charged in a glass reactor equipped with a central vertical stirrer and a vertical condenser followed by stirring at 30° C. for 4 hours to obtain a slurry. Separately, 125.00 gm of 2-cyano-2-propenoic acid ethyl ester (1 mole) was stabilized with methanesulfonic acid (3 wt %) dissolved in 100 ml of isopropanol to obtain a stabilized solution of 2-cyano-2-propenoic acid ethyl ester. The stabilized solution of 2-cyano-2-propenoic acid ethyl ester was injected into the slurry over 2 hours at 20° C. to 25° C. to obtain a reaction mixture. The reaction mixture was stirred further for 4 hours at 20° C. to 25° C. to obtain a reaction mass containing sodium salt of 2,3-dicyanopropionic acid ethyl ester. Reaction was monitored on the basis of unreacted sodium cyanide. Then the reaction mixture containing sodium salt of 2,3-dicyanopropionic acid ethyl ester was cooled to 10° C. and dry hydrogen chloride gas was bubbled to neutralize the sodium salt of 2,3-dicyanopropionic acid ethyl ester. The neutralized reaction mass was then subjected to vacuum distillation to distill isopropanol. To the crude product obtained as a residue after distillation was added methylene dichloride and water below 10° C. and extracted. The organic layer containing the product and aqueous layer were separated. The organic layer was washed with water and then concentrated to obtain 2,3-dicyanopropionic acid ethyl ester in 86% yield (on purity basis).

Example 4

2,3-dicyanopropionic Acid Ethyl Ester Using Trifluoromethane Sulfonic Acid as a Stabilizing Agent 1.0 liter of anhydrous ethanol and 100 gm of sodium cyanide (2.0 mole) were charged in a glass reactor equipped with a central vertical stirrer and a vertical condenser followed by stirring at 30° C. for 4 hours to obtain slurry. Separately, 250.00 gm of 2-cyano-2-propenoic acid ethyl ester (2 mole) was stabilized with trifluoromethane sulfonic acid (0.5 wt %) dissolved in 200 ml of ethanol to obtain a stabilized solution of 2-cyano-2-propenoic acid ethyl ester. The stabilized solution of 2-cyano-2-propenoic acid ethyl ester was injected into the slurry over 2 hours at 20° C. to 25° C. to obtain a reaction mixture. The reaction mixture was stirred further for 4 hours at 25° C. to 30° C. to obtain a reaction mass containing sodium salt of 2,3-dicyanopropionic acid ethyl ester. Reaction was monitored on the basis of unreacted sodium cyanide. Then the reaction mixture containing sodium salt of 2,3-dicyanopropionic acid ethyl ester was cooled to 10° C. and dry hydrogen chloride gas was bubbled to neutralize the sodium salt of 2,3-dicyanopropionic acid ethyl ester. The neutralized reaction mass was then subjected to vacuum distillation to distill ethanol. To the crude product obtained as a residue after distillation was added methylene dichloride and water below 10° C. and extracted. The organic layer containing the product and aqueous layer were separated. The organic layer was washed with water and then concentrated to obtain 2,3-dicyanopropionic acid ethyl ester in 81% yield.

Example: 5

0.6 liter of anhydrous dimethylsulfoxide and 51.46 gm of sodium cyanide (1.05 mole) were charged in a glass reactor equipped with a central vertical stirrer and a vertical condenser followed by stirring at 30° C. for 4 hours to obtain a slurry. Separately, 125.00 gm of 2-cyano-2-propenoic acid ethyl ester (1 mole) was stabilized with methanesulfonic acid (3 wt %) dissolved in 100 ml of anhydrous dimethylsulfoxide to obtain a stabilized solution of 2-cyano-2-propenoic acid ethyl ester. To the stabilized solution of 2-cyano-2-propenoic acid ethyl ester was added the slurry over 2 hours at 20° C. to 25° C. to obtain a reaction mixture. The reaction mixture was stirred further for 4 hours at 20° C. to 25° C. to obtain a reaction mass containing sodium salt of 2,3-dicyanopropionic acid ethyl ester. Reaction was monitored on the basis of unreacted sodium cyanide. Then the reaction mixture containing sodium salt of 2,3-dicyanopropionic acid ethyl ester was cooled to 10° C. and dry hydrogen chloride gas was bubbled to neutralize the sodium salt of 2,3-dicyanopropionic acid ethyl ester. The neutralized reaction mass was then subjected to vacuum distillation to distill dimethylsulfoxide. To the crude product obtained as a residue after distillation was added methylene dichloride and water below 10° C. and extracted. The organic layer containing the product and aqueous layer were separated. The organic layer was washed with water and then concentrated to obtain 2,3-dicyanopropionic acid ethyl ester in 78% yield (on purity basis).

Example: 6

0.6 liter of anhydrous monoglyme and 51.46 gm of sodium cyanide (1.05 mole) were charged in a glass reactor equipped with a central vertical stirrer and a vertical condenser followed by stirring at 30° C. for 4 hours to obtain a slurry. Separately, 125.00 gm of 2-cyano-2-propenoic acid ethyl ester (1 mole) was stabilized with methanesulfonic acid (3 wt %) dissolved in 100 ml of anhydrous monoglyme to obtain a stabilized solution of 2-cyano-2-propenoic acid ethyl ester. To the stabilized solution of 2-cyano-2-propenoic acid ethyl ester was added the slurry over 2 hours at 20° C. to 25° C. to obtain a reaction mixture. The reaction mixture was stirred further for 4 hours at 20° C. to 25° C. to obtain a reaction mass containing sodium salt of 2,3-dicyanopropionic acid ethyl ester. Reaction was monitored on the basis of unreacted sodium cyanide. Then the reaction mixture containing sodium salt of 2,3-dicyanopropionic acid ethyl ester was cooled to 10° C. and dry hydrogen chloride gas was bubbled to neutralize the sodium salt of 2,3-dicyanopropionic acid ethyl ester. The neutralized reaction mass was then subjected to vacuum distillation to distill monoglyme. To the crude product obtained as a residue after distillation was added methylene dichloride and water below 10° C. and extracted. The organic layer containing the product and aqueous layer were separated. The organic layer was washed with water and then concentrated to obtain 2,3-dicyanopropionic acid ethyl ester in 78% yield (on purity basis).

Example: 7

0.6 liter of anhydrous ethanol and 51.46 gm of sodium cyanide (1.05 mole) were charged in a glass reactor equipped with a central vertical stirrer and a vertical condenser followed by stirring at 30° C. for 4 hours to obtain a slurry. Separately, 125.00 gm of 2-cyano-2-propenoic acid ethyl ester (1 mole) was stabilized with methanesulfonic acid (3 wt %) dissolved in 200 ml of ethylene dichloride to obtain a stabilized solution of 2-cyano-2-propenoic acid ethyl ester. The stabilized solution of 2-cyano-2-propenoic acid ethyl ester was injected into the slurry over 2 hours at 20° C. to 25° C. to obtain a reaction mixture. The reaction mixture was stirred further for 4 hours at 20° C. to 25° C. to obtain a reaction mass containing sodium salt of 2,3-dicyanopropionic acid ethyl ester. Reaction was monitored on the basis of unreacted sodium cyanide. Then the reaction mixture containing sodium salt of 2,3-dicyanopropionic acid ethyl ester was cooled to 10° C. and dry hydrogen chloride gas was bubbled to neutralize the sodium salt of 2,3-dicyanopropionic acid ethyl ester. The neutralized reaction mass was then subjected to vacuum distillation to distill ethanol and ethylene dichloride. To the crude product obtained as a residue after distillation was added ethylene dichloride and water below 10° C. and extracted. The organic layer containing the product and aqueous layer were separated. The organic layer was washed with water and then concentrated to obtain 2,3-dicyanopropionic acid ethyl ester in 78% yield (on purity basis).

Example: 8

One Pot Preparation of 2,3-dicyanopropionic Acid Ethyl Ester 0.6 liter of anhydrous isopropanol and 51.46 gm of sodium cyanide (1.05 mole) were charged in a glass reactor equipped with a central vertical stirrer and a vertical condenser followed by stirring at 30° C. to obtain a slurry. A solution of 125.00 gm of 2-cyano-2-propenoic acid ethyl ester (1 mole) stabilized with methanesulfonic acid (3 wt %) in 200 ml of anhydrous isopropanol was added in one lot to the slurry at 20° C. to 25° C. to obtain a reaction mixture. The reaction mixture was stirred for 4 hours at 20° C. to 25° C. to obtain a reaction mass containing sodium salt of 2,3-dicyanopropionic acid ethyl ester. Reaction was monitored on the basis of unreacted sodium cyanide. Then the reaction mixture containing sodium salt of 2,3-dicyanopropionic acid ethyl ester was cooled to 10° C. and dry hydrogen chloride gas was bubbled to neutralize the sodium salt of 2,3-dicyanopropionic acid ethyl ester. The neutralized reaction mass was then subjected to vacuum distillation to distill isopropanol. To the crude product obtained as a residue after distillation was added ethylene dichloride and water below 10° C. and extracted. The organic layer containing the product and aqueous layer were separated. The organic layer was washed with water and then concentrated to obtain 2,3-dicyanopropionic acid ethyl ester in 82% yield (on purity basis).

Example: 9

0.6 liter of anhydrous ethanol and 51.46 gm of sodium cyanide (1.05 mole) were charged in a glass reactor equipped with a central vertical stirrer and a vertical condenser followed by stirring at 30° C. for 4 hours to obtain a slurry. Separately, 125.00 gm of 2-cyano-2-propenoic acid ethyl ester (1 mole) was stabilized with 60.05 gm of acetic acid (1 mole) dissolved in 200 ml of ethylene dichloride to obtain a stabilized solution of 2-cyano-2-propenoic acid ethyl ester. The stabilized solution of 2-cyano-2-propenoic acid ethyl ester was injected into the slurry over 2 hours at 20° C. to 25° C. to obtain a reaction mixture. The reaction mixture was stirred further for 4 hours at 20° C. to 25° C. to obtain a reaction mass containing sodium salt of 2,3-dicyanopropionic acid ethyl ester. Reaction was monitored on the basis of unreacted sodium cyanide. Then the reaction mixture containing sodium salt of 2,3-dicyanopropionic acid ethyl ester was cooled to 10° C. and pH was adjusted to 5 by adding acetic acid. The acidic reaction mass was then subjected to vacuum distillation to distill ethanol and ethylene dichloride. To the crude product obtained as a residue after distillation was added methylene dichloride and water below 10° C. and extracted. The organic layer containing the product and aqueous layer were separated. The organic layer was washed with water and then concentrated to obtain 2,3-dicyanopropionic acid ethyl ester in 78% yield (on purity basis).

Example 10

Anhydrous ethanol (0.6 lits) and 51.46 gm of sodium cyanide (1.05 mole) were charged in a glass reactor having a central vertical stirrer and a vertical condenser to obtain a slurry. The obtained slurry was stirred at 30° C. for 4 hrs. Separately, 125.0 gm of ethyl-2-cyano-2-propenoic acid ester (1 mole) was stabilized with 3 wt. % methane sulfonic acid (MSA) dissolved in 100 ml of ethanol to obtain a stabilized solution of 2-cyano-2-propenoic acid ethyl ester. The stabilized solution of 2-cyano-2-propenoic acid ethyl ester was injected into the slurry over 2 hours with maintenance of temperature of 20-25° C. The obtained reaction mixture was stirred at 20-25° C. for 4 hours to obtain a reaction mass containing sodium salt of 2,3-dicyanopropionic acid ethyl ester. Reaction was monitored on the basis of unreacted sodium cyanide. The reaction mass was cooled to 10° C. and dry HCl was bubbled to neutralize sodium salt of 2,3-dicyanopropionic acid ethyl ester. The neutralized mass was then subjected to vacuum distill ethanol. To the crude product was added 300 ml Toluene/water at <10° C. to separate the layers. Aqueous layer was extracted with additional 300 ml toluene. The organic layer was washed with water & then concentrated to get 85% yield (on purity basis).

Technical Advancement and Economic Significance:

The present process for preparing 2,3-dicyanopropionic acid esters is simple and economic.

The present process for preparing 2,3-dicyanopropionic acid esters is high yielding.

The present process provides highly pure 2,3-dicyanopropionic acid esters.

The present process employs stable reactants.

The present process is single pot reaction.

While considerable emphasis has been placed herein on the specific steps of the preferred process, it will be appreciated that many steps can be made and that many changes can be made in the preferred steps without departing from the principles of the invention. These and other changes in the preferred steps of the invention will be apparent to those skilled in the art from the disclosure herein, whereby it is to be distinctly understood that the foregoing descriptive matter is to be interpreted merely as illustrative of the invention and not as a limitation.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

The numerical values mentioned for the various physical parameters, dimensions or quantities are only approximations and it is envisaged that the values higher/lower than the numerical values assigned to the parameters, dimensions or quantities fall within the scope of the invention, unless there is a statement in the specification specific to the contrary.

The invention claimed is:

1. A process for preparing 2,3-dicyanopropionic acid ester of formula (I); said process comprising the following steps:
   i) providing a slurry of sodium cyanide in a solvent and reacting with a solution of 2-cyano-2-propenoic acid ester of formula (II) which is pre-stabilized using a stabilizing agent at a temperature ranging between 0° C. and 50° C. for a time period ranging between 2 hours and 15 hours followed by cooling below 20° C. to obtain a sodium salt of 2,3-dicyanopropionic acid ester of formula (I);

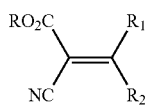

wherein, R is selected from the group consisting of $C_1$-$C_4$ straight or branched chain alkyl substituents and substituted or unsubstituted aromatic substituents; and $R_1$ and $R_2$ are hydrogen, ii) neutralizing the sodium salt of 2,3-dicyanopropionic acid ester using a neutralizing agent to obtain a 2,3-dicyanopropionic acid ester of formula (I),

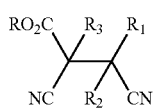

wherein, R is selected from the group consisting of $C_1$-$C_4$ straight or branched chain alkyl substituents and substituted or unsubstituted aromatic substituents;

$R_1$ and $R_2$ are hydrogen; and $R_3$ is hydrogen.

2. The process for preparing 2,3-dicyanopropionic acid ester of formula (I) as claimed in claim 1; said process comprising the following steps:

a. adding sodium cyanide to a solvent followed by stirring at a temperature ranging between 0° C. and 50° C. for a time period ranging between 2 hours and 8 hours to obtain a slurry;

b. injecting a solution of 2-cyano-2-propenoic acid ester of formula (II) which is pre-stabilized using a stabilizing agent into the slurry at a temperature ranging between 0° C. and 50° C. for a time period ranging between 2 hours and 8 hours to obtain a reaction mixture;

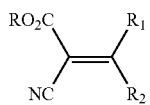

wherein, R is selected from the group consisting of $C_1$-$C_4$ straight or branched chain alkyl substituents and substituted or unsubstituted aromatic substituents; and $R_1$ and $R_2$ are hydrogen, c. stirring the reaction mixture at a temperature ranging between 0° C. and 50° C. for a time period ranging between 2 hours and 15 hours followed by cooling below 20° C. to obtain a sodium salt of 2,3-dicyanopropionic acid ester of formula (I); and d. neutralizing the sodium salt of 2,3-dicyanopropionic acid ester using a neutralizing agent to obtain a 2,3-dicyanopropionic acid ester of formula (I),

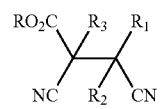

wherein, R is selected from the group consisting of $C_1$-$C_4$ straight or branched chain alkyl substituents and substituted or unsubstituted aromatic substituents;

$R_1$ and $R_2$ are hydrogen; and $R_3$ is hydrogen.

3. The process as claimed in claim 1, further comprising the step of adding a slurry containing sodium cyanide into the solution of 2-cyano-2-propenoic acid ester of formula (II) at a temperature ranging between 0° C. and 50° C. for a time period ranging between 2 hours and 8 hours.

4. The process as claimed in claim 1, wherein the stabilizing agent is at least one selected from the group consisting of methanesulfonic acid, methanesulfonic anhydride, trifluoromethane sulfonic acid, trifluoromethane sulfonic anhydride, trichloromethane sulfonic acid, trichloromethane sulfonic anhydride, tribromomethane sulfonic acid, tribromomethane sulfonic anhydride, substituted or unsubstituted aromatic sulfonic acids, substituted or unsubstituted aromatic sulfonic anhydrides, hydroquinone, alkyl substituted hydroquinone, phosphorous pentoxide and $C_1$-$C_{14}$ aliphatic carboxylic acids.

5. The process as claimed in claim 1, wherein the amount of stabilizing agent ranges between 0.1 and 15% of the mass of 2-cyano-2-propenoic acid ester of the formula (II).

6. The process as claimed in claim 1, wherein the proportion of the solvent ranges between 500 ml and 1000 ml per mole of 2-cyano-2-propenoic acid ester of formula (II).

7. The process as claimed in claim 1, wherein the neutralizing agent is at least one selected from the group consisting of hydrogen chloride, $C_1$-$C_{14}$ aliphatic acids and aromatic acids.

8. The process as claimed in claim 1, wherein the 2-cyano-2-propenoic acid ester of formula (II) is selected from the group consisting of 2-cyano-2-propenoic acid methyl ester, 2-cyano-2-propenoic acid ethyl ester, 2-cyano-2-propenoic acid isopropyl ester and 2-cyano-2-propenoic acid propyl ester.

9. The process as claimed in claim 1, wherein the 2,3-dicyanopropionic acid ester of formula (I) is selected from the group consisting of 2,3-dicyanopropionic acid methyl ester, 2,3-dicyanopropionic acid ethyl ester, 2,3-dicyanopropionic acid isopropyl ester and 2,3-dicyanopropionic acid propyl ester.

* * * * *